United States Patent
Payne et al.

(10) Patent No.: US 11,543,037 B2
(45) Date of Patent: Jan. 3, 2023

(54) METASTABLE STATE OF DUAL LATCHING VALVES

(71) Applicant: SFC Fluidics, Inc., Fayetteville, AR (US)

(72) Inventors: Forrest W. Payne, Fayetteville, AR (US); Bradley Ledden, Fayetteville, AR (US); Gil Kan, Alpharetta, GA (US); Greg Lamps, Smyrna, GA (US)

(73) Assignee: SFC Fluidics, Inc., Fayetteville, AR (US)

( * ) Notice: Subject to any disclaimer, the term of this patent is extended or adjusted under 35 U.S.C. 154(b) by 56 days.

(21) Appl. No.: 17/271,247

(22) PCT Filed: Aug. 29, 2019

(86) PCT No.: PCT/US2019/048777
§ 371 (c)(1),
(2) Date: Feb. 25, 2021

(87) PCT Pub. No.: WO2020/047235
PCT Pub. Date: Mar. 5, 2020

(65) Prior Publication Data
US 2021/0341065 A1     Nov. 4, 2021

Related U.S. Application Data

(60) Provisional application No. 62/724,933, filed on Aug. 30, 2018.

(51) Int. Cl.
*F16K 7/06* (2006.01)
*F16K 7/04* (2006.01)
(Continued)

(52) U.S. Cl.
CPC ............. *F16K 7/065* (2013.01); *F16K 7/045* (2013.01); *F16K 11/027* (2013.01);
(Continued)

(58) Field of Classification Search
CPC ........ F16K 7/065; F16K 7/045; F16K 11/027; F16K 11/044; F16K 99/0026;
(Continued)

(56) References Cited

U.S. PATENT DOCUMENTS 2,556,689 A  *  6/1951  Grove .................... F16K 7/065
                                                               251/7
3,411,534 A  * 11/1968  Rose ..................... A61M 39/28
                                                              604/32
(Continued)

FOREIGN PATENT DOCUMENTS

EP           3202441 A1  *  8/2017  .......... A61M 39/223
EP           3202441 B1    11/2021
(Continued)

OTHER PUBLICATIONS

EPO search report for application No. 19855275.4, dated May 9, 2022.

*Primary Examiner* — Craig J Price
*Assistant Examiner* — Andrew J Rost

(57) ABSTRACT

A dual latching microvalve is capable of a metastable state, wherein a one or more complete flow paths are open, before switching to another state that allows only an inlet or outlet valve to be open at any time on any fluid path. One valve mechanism uses a cam to alternately open and close two valves, with an external force applying pressure to move one valve arm onto a resting position on the cam, thereby opening the closed valve and provided an uninterrupted flow path through the dual latching microvalve. The metastable state provides, for example, a means to prime the pump before operation, such as pumping of insulin into a patient. When released from the metastable state, the dual latching microvalve operates in a fashion whereby opening of both valves simultaneously is prevented, thereby protecting the patient from injury.

24 Claims, 8 Drawing Sheets

(51) Int. Cl.
*F16K 11/02* (2006.01)
*F16K 99/00* (2006.01)

(52) U.S. Cl.
CPC ...... *F16K 99/0026* (2013.01); *F16K 99/0038* (2013.01); *F16K 2099/0069* (2013.01); *F16K 2099/0071* (2013.01)

(58) Field of Classification Search
CPC ......... F16K 99/0038; F16K 2009/0069; F16K 2009/0071; F16K 31/025; F16K 7/063; A61M 2205/0294
See application file for complete search history.

(56) References Cited

U.S. PATENT DOCUMENTS

| | | | | |
|---|---|---|---|---|
| 3,754,768 | A * | 8/1973 | Ellis | B60G 17/0525 137/625.2 |
| 3,861,421 | A | 1/1975 | Thompson | |
| 3,918,490 | A * | 11/1975 | Goda | F16K 7/065 137/597 |
| 4,282,902 | A * | 8/1981 | Haynes | F16K 7/065 251/297 |
| 4,653,719 | A * | 3/1987 | Cabrera | F16K 11/027 251/5 |
| 4,691,738 | A * | 9/1987 | McCune | F16K 11/027 251/9 |
| 2003/0234053 | A1 * | 12/2003 | Hampsch | F16K 11/027 137/595 |
| 2014/0103142 | A1 | 4/2014 | Butts | |
| 2017/0120039 | A1 | 5/2017 | Childs et al. | |
| 2017/0224918 | A1 | 8/2017 | Payne et al. | |
| 2017/0321810 | A1 | 11/2017 | Geiger | |
| 2018/0245699 | A1 | 8/2018 | Lee | |

FOREIGN PATENT DOCUMENTS

| | | |
|---|---|---|
| JP | S6073176 A | 4/1985 |
| WO | 2009149137 A1 | 12/2009 |

* cited by examiner

US 11,543,037 B2

METASTABLE STATE OF DUAL LATCHING VALVES

CROSS-REFERENCE TO RELATED APPLICATIONS

This application claims the benefit of US provisional patent application no. 62/724,933 filed on Aug. 30, 2018 and entitled Cam Valve Mechanism. Such application is incorporated herein by reference in its entirety.

STATEMENT REGARDING FEDERALLY SPONSORED RESEARCH OR DEVELOPMENT

This invention was made with government support under Grant Number 2R44DA041173-02 awarded by the National Institute on Drug Abuse at the National Institutes of Health.

BACKGROUND OF THE INVENTION

The invention relates to valves for fluidic devices, particularly to valves that rest in a metastable state where one or more complete fluid paths are open before switching to a stable state that allows only one inlet or outlet valve on a fluid path to be open at a time.

Fluidic microvalves can be constructed of cantilevered spring arms squeezing a compressible tube. U.S. Pat. No. 3,335,753 teaches a pinch valve consisting of a lever arm actuated preferably by a solenoid, but alternatively by a cam, that pinches a soft tube. U.S. Pat. No. 9,067,051 teaches a microfluidic pinch valve consisting of cantilevered arms squeezing a compressible tube where compression force is provided by an actuator. Actuator mechanisms such as magnetic, piezoelectric, pneumatic, and mechanical are mentioned. This patent makes no mention, however, of valves synchronized such that closing one fluid path allows for the opening of another flow path. International Patent App. No. PCT/US2015/045251 teaches a dual latching microvalve wherein both valves close momentarily before one valve opens. This application makes no mention of initially positioning the dual latching valves in a metastable state permitting both inlet and outlet fluid paths to be open to allow for fill and priming of the fluidic network. U.S. patent application Ser. No. 16/436,627 teaches of a dual latching cam microvalve comprised of a cam that when rotated causes a valve arm to either pinch or un-pinch a compressible tube. No specification of cam shape is made, nor is there any mention of a metastable state permitting flow through both fluid paths.

BRIEF SUMMARY OF THE INVENTION

The present invention is directed to dual latching microvalves capable of a metastable state where one or more complete fluid paths are open before switching to a stable state that allows only one inlet or outlet valve on a fluid path to be open at a time. Because one embodiment of the present invention involves a new feature of dual latching valves, normal operation of these valves will be described first, followed by differentiation of the present invention. Normal operation of the dual latching valves is the stable state. One important application of dual latching microvalves is metered control of fluid flow from a large reservoir into a smaller reservoir and then to the outlet. One valve (the inlet valve) of the set of dual latching valves is between the large reservoir and the small metering reservoir and the second valve (the outlet valve) of the set is between the metering reservoir and the outlet. A set of dual latching microvalves work in concert such that one valve is always latched closed when the other valve is open, which prevents an open pathway from the reservoir to the outlet. A valve mechanism controls operation of the two valves and physically prevents them from being open at the same time. The benefits of such an arrangement become apparent when used in on-body drug delivery pods. An example is insulin delivery where contents of the reservoir could be fatal if accidentally delivered all at once. This danger can be mitigated using a set of dual latching microvalves and a much smaller, intermediate metering chamber.

The cam embodiments of dual latching microvalves are constructed using a cam as the valve mechanism so that rotation of a single cam controls the timing of opening and closing of the inlet and outlet valves such that both valves are closed temporarily before one of the valves is opened. In certain implementations, the valve mechanism is actuated by passing a current through a shape memory alloy (SMA) wire, causing the wire to heat and contract. The wire rotates the cam which pinches a resilient compressible tube stopping flow, or releases the tube permitting flow. This can be achieved with the cam directly or using a cam follower, such as a valve end, that compresses and releases the resilient tubing.

One non-limiting application of the cam embodiment of a dual latching microvalve is in drug delivery (for example insulin) using an electrochemiosmotic reciprocating pump with a built-in metering chamber. The cam-controlled dual-latching microvalves provide an important safety feature as the coordinated operation of the pump inlet and outlet valves prevent an open line between reservoir and patient.

The present invention provides for a metastable state for the dual latching microvalves that is in direct contradiction to the stable operating state where only one valve is open at a time. The metastable state uses an interference mechanism to intentionally allow both valves to open at the same time, providing a direct fluid path from the reservoir to the outlet (i.e. both valves are open at once) so that the entire fluid path can be easily primed with solution prior to stable operation. The metastable state permits easy filling of the fluidic system.

Alterations to a standard dual-latching cam microvalve that allow for a metastable state out of the plane of the valve seat can include a valve arm comprising a valve arm end that returns to a stable state after being held in the metastable state, shaping of the cam to create a space for the valve arm end to move into position for normal operation under its own resilience, a slope to the cam and or valve arm end that allows for the valve arm end to slide easily into position for normal operation and a raised edge on the surface of the cam or the valve arm end to help hold the valve arm end in the metastable state during storage. Other interference mechanisms besides a cam can also possess these features for the creation of a metastable state.

Other embodiments could include a pin or other removeable structure that would hold the valve arm end in the metastable state. Alternatively, the metastable state can be obtained with the valve arm in the plane of the valve seat by temporarily creating a gap on either side of the compressible tube that prevents the valve arm end from compressing the tube against the valve seat. In this case, the temporary gap is closed after prime and flush of the fluid line. These and other features, and advantages of the present invention will become better understood from a consideration of the following detailed description and drawings as follows:

DETAILED DESCRIPTION OF THE PREFERRED EMBODIMENT(S)

Before the present invention is described in further detail, it should be understood that the invention is not limited to the particular embodiments described, and that the terms used in describing the particular embodiments are for the purpose of describing those particular embodiments only, and are not intended to be limiting, since the scope of the present invention will be limited only by the claims.

As in the Brief Summary of the Invention, stable operation of dual latching valves will be described first (FIGS. 1-3) followed by a description of the present invention: the metastable state of dual latching valves (FIGS. 4-8). Although the focus of this description is on the metastable state of dual latching cam microvalves, embodiments can be envisioned for other types of dual latching valves.

Figure 1:
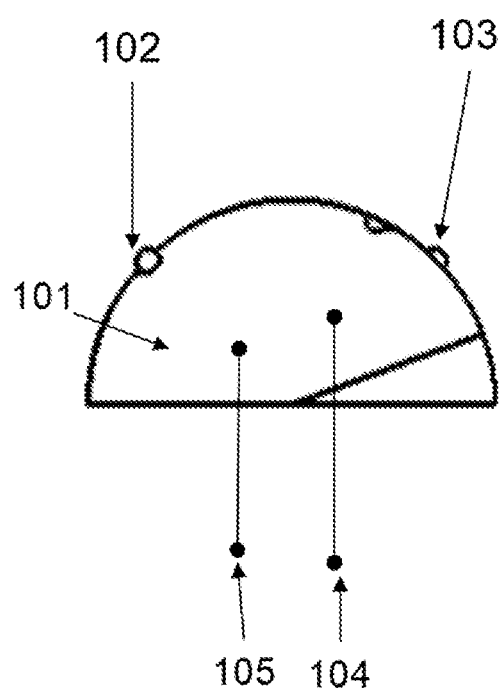
FIG. 1 depicts a dual latching cam valve in a first orientation according to stable operation (prior art).
Figure 2:
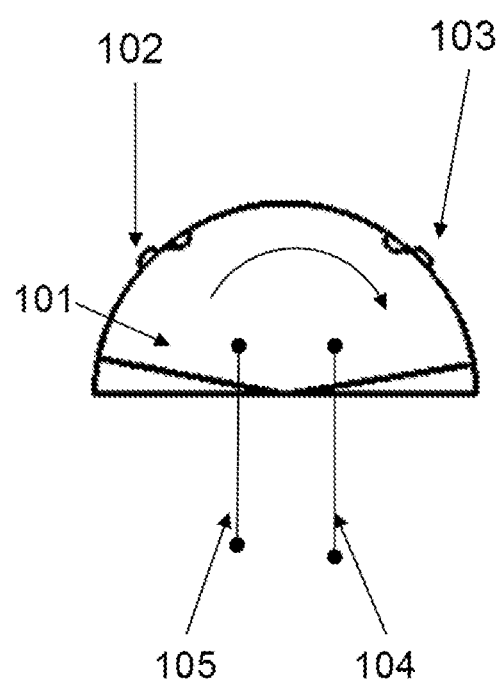
FIG. 2 depicts a dual latching cam valve in a second orientation according to stable operation (prior art).

The dual latching valve can be designed in different ways. FIG. 1 depicts the valve mechanism as a cam that is a rotating semi-circular disk 101 that acts to alternatively pinch two flexible tubes 102, 103. The cam valve wheel is rotated by actuation of the Shape Memory Alloy (SMA) wires 104, 105 which have one end attached to the cam and the other attached to the base. FIG. 1 illustrates the cam in a stable operational state, wherein the left side tube 102 is open and the right-side tube 103 is pinched shut. The valve can stay in this state indefinitely and requires no power. When electric current passes through the right SMA wire 104 the wire contracts and the cam rotates clockwise. During clockwise rotation, the cam's profile continues pinching the right tube 103 and begins pinching the left tube 102. As the cam continues to rotate clockwise, both fluid paths 102, 103 are closed as shown in FIG. 2. Upon completion of the clockwise rotation, the right fluid path 103 is open and the left fluid path 102 is closed. The valve is stable in this state indefinitely and requires no power. Rotation of the cam in the counterclockwise direction is prevented by the friction of the assembly. To switch the valve back to state 1, the left SMA wire 105 is heated by the flow of electricity. As the left SMA wire 105 contracts, it both rotates the cam 101 counterclockwise and stretches the right SMA wire 104. After counterclockwise rotation, the left fluid path 102 is open and the right fluid path 103 is closed, and the valve is returned to the original state in FIG. 1. The cam is stable in this position until the right SMA wire 104 is energized. In summary, only one tube is open at a time preventing an open path between reservoir and patient. This significant safety feature prevents accidental overdose even in the case of device failure when used as a medicament delivery device for a patient.

Figure 3:
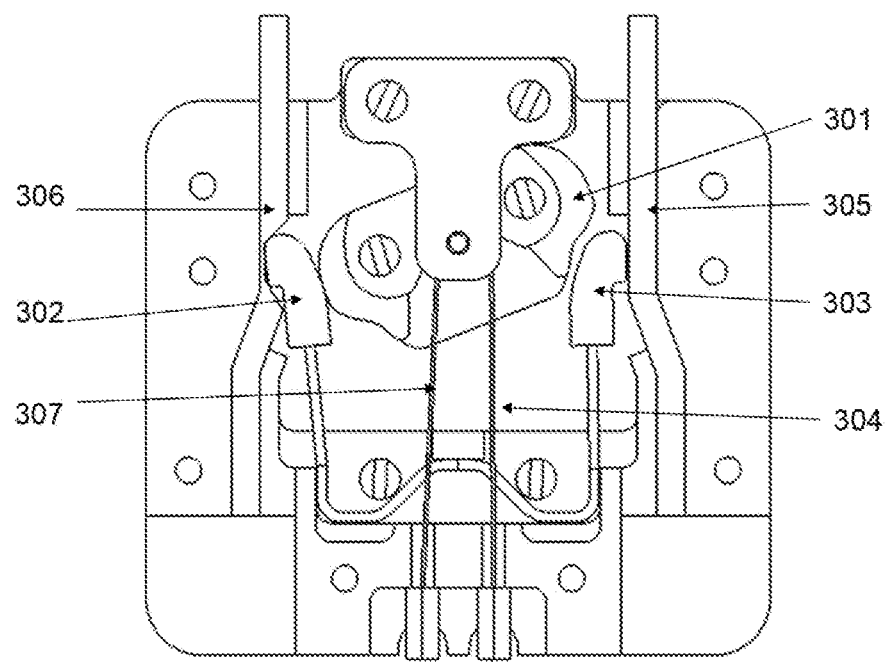
FIG. 3 depicts one type of dual latching cam valve using compressible tubing and valve arms showing stable operation where only one fluid path is open (prior art).

In the previously described dual latching cam valve, the tube contact profile was on the circumference of the semi-circular disk 101. Another type of dual latching cam valve, shown in FIG. 3, uses a cam with a varying radius 301 which displaces cam following valve arms 302, 303. The cam 301 may be actuated by the SMA wires 304, 307 and use a cam follower attached, or integral, to a flexible beam to compress the tubing. When electric current passes through the right SMA wire 304, the wire contracts, and the cam 301 rotates clockwise. Clockwise rotation pushes the right valve arm 303 to the right, pinching the right tube 305 to prevent fluid flow. Meanwhile, the left valve arm 302 is free to move to the right to its relaxed position allowing the left tube 306 to open, permitting fluid flow. In FIG. 3 both valve arms 302, 303 are made from spring wire, though plastic or other materials could be used. The beams are capped with a plastic valve head to create a flat smooth surface for compressing the flexible tubes. The tube orientation relative to the valve arm can be in different orientations so long as the head of the valve arm can compress the tube to stop flow When the left SMA wire 307 is energized, it contracts, rotating the cam 301 counterclockwise. After passing through the interim position, where both tubes 305 and 306 are pinched shut similar to the condition in FIG. 2, the cam will rest in a state in which the left tube 306 is compressed closed, and the right tube 305 is open. As depicted in FIG. 3 the cam rotation can be accomplished by SMA wires but it is not limited to this type of actuation and it can be achieved by any actuator that will cause the cam to rotate such as a motor, gear, magnet, or other method.

Figure 4:
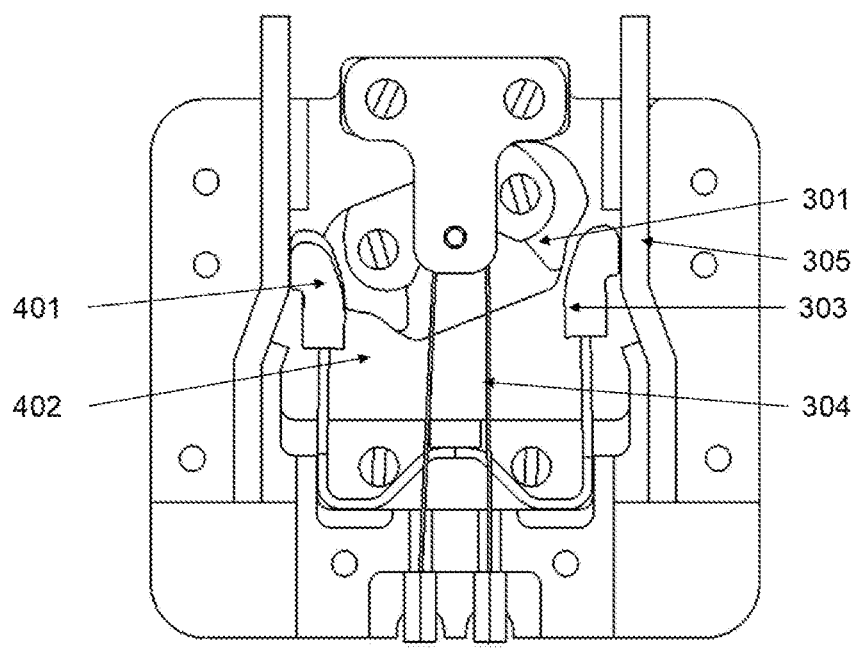
FIG. 4 depicts one embodiment of the dual latching cam valve of FIG. 3 with a valve arm in a metastable state permitting flow through both fluid paths.

FIG. 4 depicts one embodiment of the current invention showing one valve arm in a metastable state with both valves open. In FIG. 4 the cam 301 is rotated to its counterclockwise position and the left resilient valve arm 401 is placed on the cam 301 where it remains under its own resilient force, leaving both sides open to flow. Having both sides open to flow is preferred during fluid loading and priming of the system. No power is required to remain in the metastable state. When the right SMA wire 304 is activated in this embodiment, the cam 301 will rotate clockwise first compressing the right tube 305 to close the valve. Further clockwise rotation will move the cam from under the left resilient valve arm 401 allowing it to transition to a stable operation position under its own resilience. In this non-limiting embodiment, 11° of clockwise rotation of the cam 301 will pinch the right tube 305 shut and at 14° of clockwise rotation the resilient valve arm 401 will be freed to enter the stable operating position.

The valve is then in the normal operational state with only one valve open to flow. Operation would then proceed as normal with the cam valve mechanism closing both valves before permitting a single open valve. After activation, when the resilient valve arm 401 enters the stable position, the valve cannot be placed back into the metastable state without an external force perpendicular to the direction of movement in the valve. The resilient force of the left valve arm presses the valve end down on the valve base 402. Please note that the cam is shaped so that it provides space for the left resilient valve arm 401 to return to the stable operating position upon clockwise rotation. In this embodiment, the width of the head of the resilient valve arm is 1.0 mm and the notch in the cam can accommodate a valve head of 1.15 mm, ensuring that the resilient valve arm has sufficient room to begin stable operation when the metastable state is terminated. Either arm can be used for the metastable state, indeed the metastable state could be chosen at different cam positions based on cam and valve arm profile chosen.

In a non-limiting example, a drug delivery device with this dual latching valve could be placed in the metastable state during assembly. The valve would be stored in this state, permitting the user to easily fill the pod since there would not be an obstruction preventing air or fluid from escaping during filling. After filling, valve activation would transition the pod to a safe condition precluding an open path between reservoir and patient.

Improvements can be made to the drawing in FIG. 4 such that the metastable state would be more secure, such as a lip or a grove on the cam or valve arm end which would prevent the metastable state from terminating, for example, during shipping. Additionally, a taper could be added to the cam or valve arm end to ensure proper placement when the metastable state is terminated.

In other embodiments, a valve arm may be moved perpendicularly to the plane of a valve and placed on an interference mechanism that is not a cam, but that would still move out of the way upon activation of the valve. In this case, the resilience of the valve arm would move it back into the plane of the valve once the interfering mechanism had been moved through initial activation of the valve, terminating the metastable state.

Figure 5:
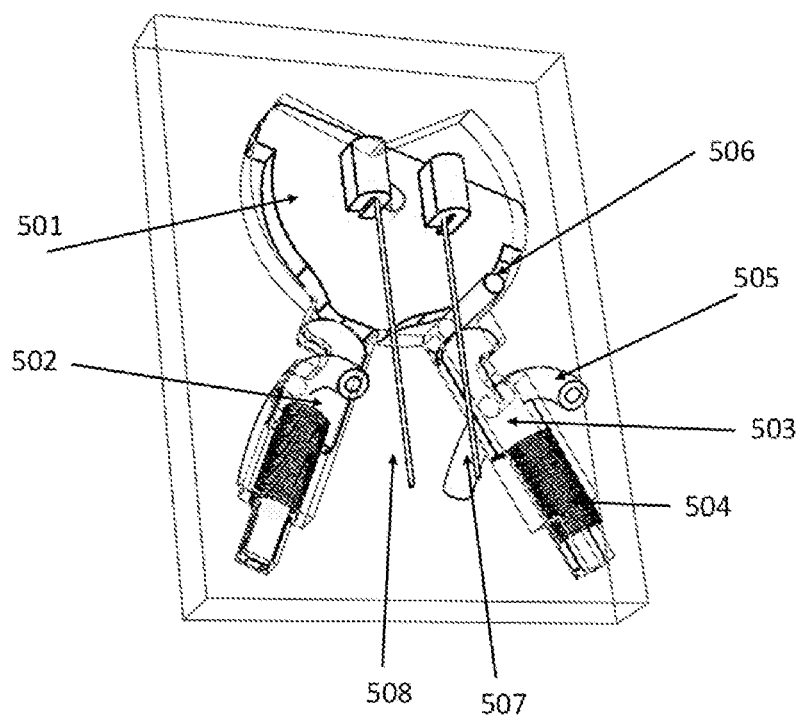
FIG. 5 depicts another embodiment of the dual latching cam valve in a metastable state with a removeable pin holding the valve in that state.

In another embodiment, the interference mechanism may be a removeable pin or other obstruction that could be used to create a metastable state, as show in FIG. 5. In this figure the cam 501 is designed so that the cam lobes push the valve arms into an open position, as opposed to the valves shown in FIGS. 3 and 4. In FIG. 5, the cam is positioned so that the left valve arm 502 is in the open position and the right valve arm 503 would be in the closed position under stable operation. The restoring spring 504 would normally push the right valve arm 503 to compress the right tube 505, however, that action is prevented by the presence of a removeable pin 506 that maintains the metastable state. Once the pin is physically removed, the right restoring spring 504 would push the right valve arm 503 to compress the tube 505. From that point on, coordinated activation of the right SMA wire 507 and left SMA wire 508 would rotate the cam for stable operation of the dual latching valve. If it is desirable to return the right valve arm 503 back to the metastable state, the pin 506 could be placed back into position.

Another implementation can be set forth where the valve seat is located on a bi-stable membrane, spring wire, flexible beam, or is otherwise moveable. This embodiment would act in a similar fashion. For example, in a metastable state, a first valve seat is set away from the first tube, so that the first tube will no longer be pinched when the first valve arm is in a normally closed position. Once the first valve seat enters its stable position, the dual latching valve would initiate its normal operation.

Figure 6:
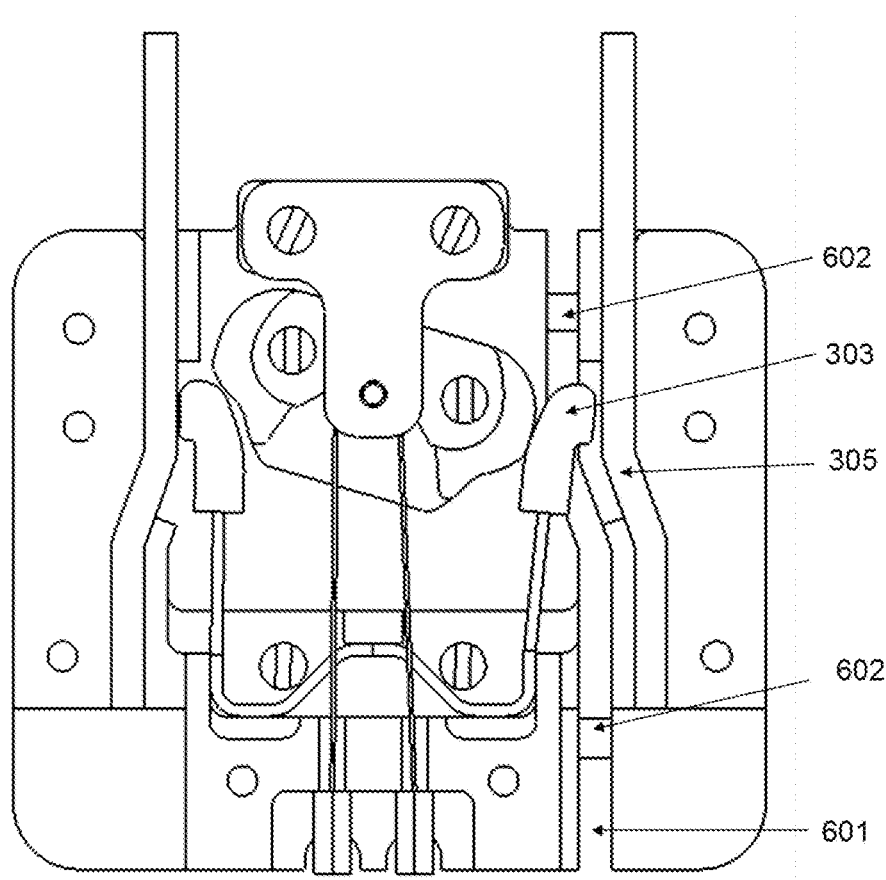
FIG. 6 depicts another embodiment of the dual latching cam valve in a metastable state with a slidable wall that prevents the closure of one valve.

An embodiment of a valve seat in a metastable state is shown in FIG. 6. In this embodiment, the dual latching valve set is initially in the metastable state with a gap 601 that prevents pinching of the right tube 305 by the right valve arm 303 even though the cam is rotated clockwise in the closed position. This allows both fluid paths to be open for priming of the fluid network. After priming, the metastable state is deactivated by closing the gap along the latching slides 602, which will result in pinching of the right tube 305 and stable operation of the dual latching cam valve.

For any of the described cam valves, in addition to friction holding the cam in a stable position, it is envisioned that a mechanism with a notch, spring fingers, detent, or other methods can be utilized to hold the cam in specific positions unless the cam is actuated intentionally.

Figure 7:
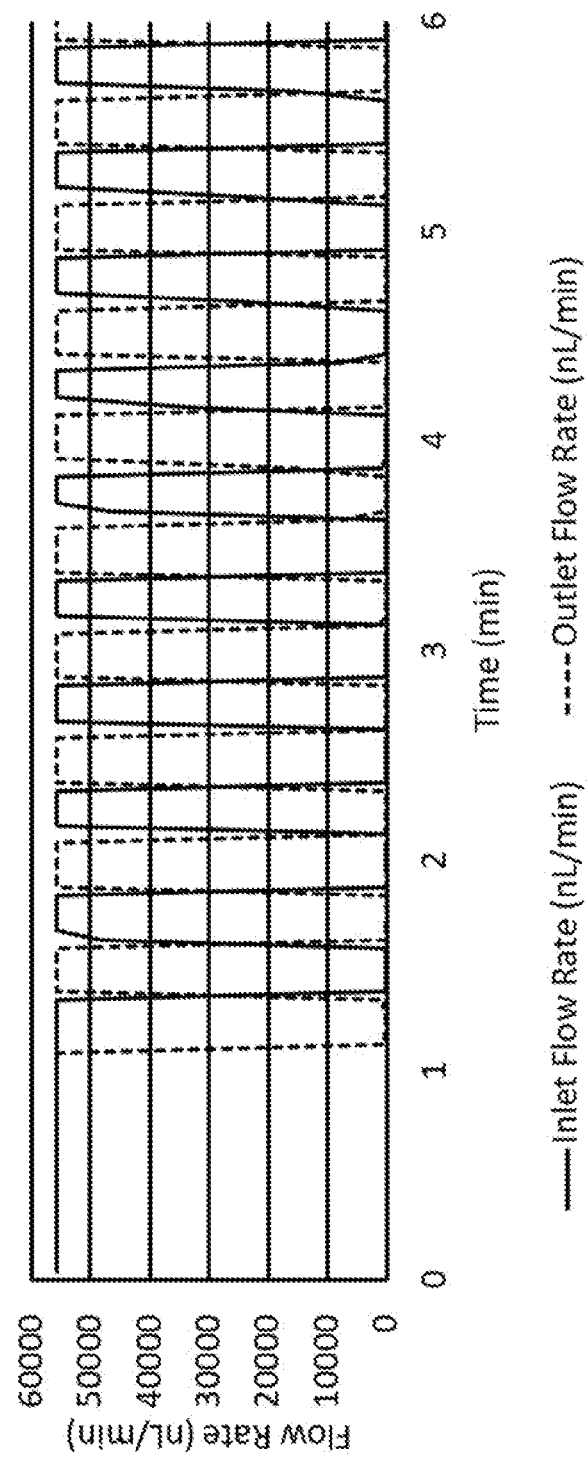
FIG. 7 is a graph illustrating the results of opening and closing a dual latching cam valve in an experimental run. At times 0 through 1 minute, the graph demonstrates the metastable state as both fluid paths are open.

Results for control of fluid flow using a prototype cam valve are presented in the graph of FIG. 7. The graph shows that both fluid paths are open at the beginning of the test. The test setup consists of a flask with water and two tubes, each having one end submerged in the water, with each tube passing through one of the flow paths of the valve. A Sensirion flow sensor is attached to each flow path and configured to measure the flow of water through the valve. A measured flow rate of approximately 55,000 nL/min indicates unobstructed flow. Both flow paths are filled with liquid and the flask is raised, establishing a siphon from the flask, through both paths of the valve, and through the flow sensors. Flow rate data for both fluid paths is shown in FIG. 7 represented as dotted and solid lines. The dual latching valve was left in the metastable state for approximately 1 minute and shows flow through both paths. Activation of one SMA wire switched the dual latching cam valve to normal operation and closed the first fluid path (dotted line). After approximately 20 seconds the other SMA wire was activated causing the second path to close (solid line) followed by opening of the first path (dotted line). Also shown is that opening of one fluid path is accompanied by closing of the other path after the initial metastable state is terminated.

Figure 8:
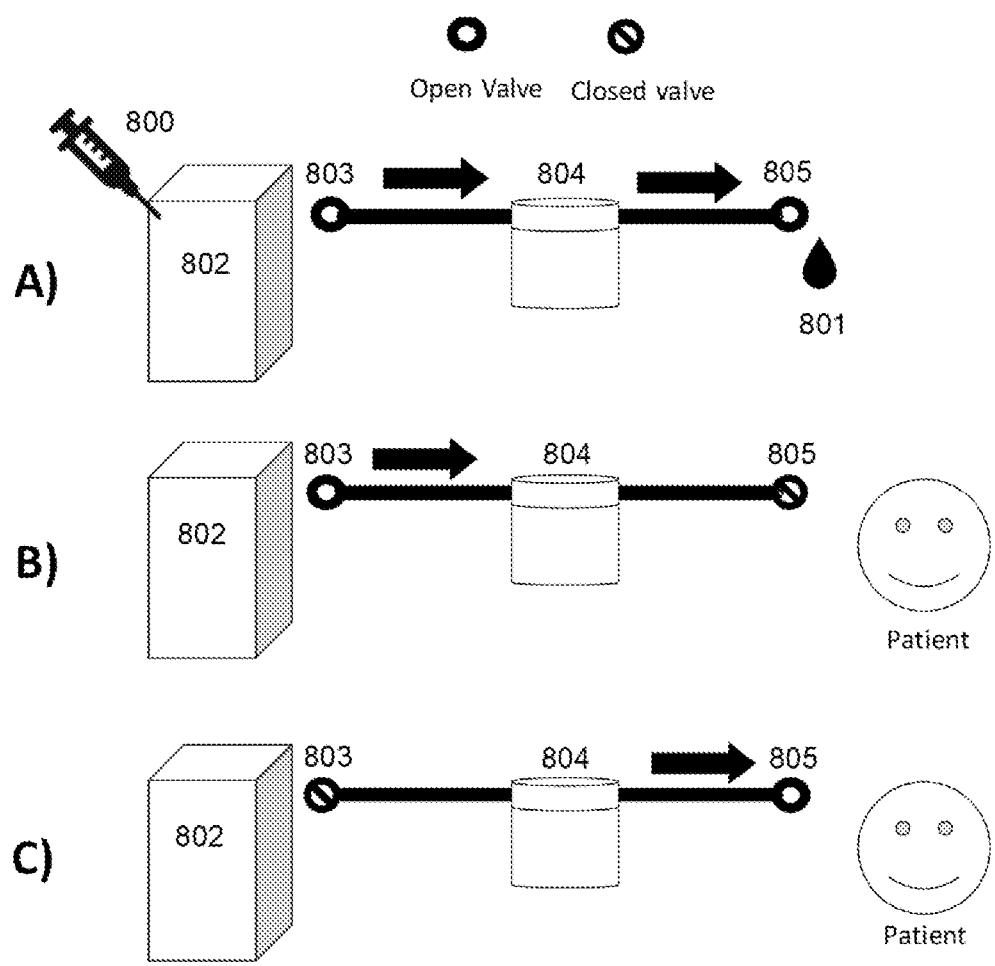
FIG. 8 is a depiction of the operation of a dual latching microvalve in A) a metastable state for reagent loading, followed by activation of the valve for normal operation, wherein B) fluid is loaded into a metering chamber and C) fluid from the metering chamber is delivered to the patient.

In a simple embodiment of a fluid delivery device using a dual latching microvalve, a single set of dual latching microvalves is used to control the flow of fluid from a reservoir into a metering chamber of a reciprocating displacement pump and then from the pump into the target application (insulin to a patient for example). This is illustrated in FIG. 8. Initially with the valve in a metastable storage state FIG. 8A, a syringe 800 is used to prime the reservoir and the fluid path with insulin 801. This can be accomplished by loading drug into a syringe 800 and then injecting the insulin 801 through a resealable septum into the reservoir 802, through the open the inlet valve 803, pump metering chamber 804, and open outlet valve 805. A user would know that the system had been primed when a drop of insulin 801 exits the system. The valve would then be activated, terminating the metastable state and the system could be attached to the patient. FIGS. 8 B and C then show normal operation of the dual latching valves where only one fluid path is open at a time. FIG. 8B shows fluid flowing through the open valve 803 into the metering chamber 804, further flow is then stopped by the closed valve 805. The dual latching valves are then switched to the position shown in FIG. 8C and the dose is safely delivered from the metering chamber 804 out through the open valve 805 and delivered to the patient.

In another pumping scheme, two dual latching microvalves could be employed, either to allow continuous flow from a two-sided electrochemiosmotic pump such as the ePump from SFC Fluidics, Inc., or to independently control fluid from both sides of an ePump to deliver two drugs (e.g., Insulin and Glucagon). In this embodiment with two sets of dual latching microvalves, both valve sets would be assembled in a metastable state permitting easy fluidic priming (drug loading) by the patient. Alternatively, a single cam (or other valve mechanism) could control fluid flow through two inlet and two outlet ports to allow continuous flow using a dual sided ePump. In this case, a single rotation of the cam would terminate the metastable state of two valve sets. Further variations on this theme can be expanded to encompass multiple inlet and outlet valves as well.

Many parts of the description herein refer to Shape Memory Alloy (SMA) wire as the actuation mechanism to terminate the metastable state and operate the valve normally. Cam actuation may also be accomplished by other methods such as motors, gears or linear actuators.

Many parts of the description herein refer to a cam as the valve mechanism that controls two or more valves. There are many designs using various types of valve mechanisms that can also create the required latching between the two valves so that they can never be open at the same time in a normal operating position.

Unless otherwise stated, all technical and scientific terms used herein have the same meaning as commonly understood by one of ordinary skill in the art to which this invention belongs. Although any methods and materials similar or equivalent to those described herein can also be used in the practice or testing of the present invention, a limited number of the exemplary methods and materials are described herein. It will be apparent to those skilled in the art that many more modifications are possible without departing from the inventive concepts herein.

All terms used herein should be interpreted in the broadest possible manner consistent with the context. All references cited herein are hereby incorporated by reference to the extent that there is no inconsistency with the disclosure of this specification. If any range is specified herein, the intention is to specifically disclose all sub-ranges within the range and all specific points within the range.

The present invention has been described with reference to certain preferred and alternative embodiments that are intended to be exemplary only and not limiting to the full scope of the present invention.

What is claimed is:

1. A method for providing flow through a single flow path using a dual latching valve operable in a metastable state, wherein the dual latching valve comprises a first tube and adjacent first arm to form a first valve, and a second tube and adjacent second arm to form a second valve, the method comprising the steps of:
    a) applying a first force to either of the first or second arms, wherein the dual latching valve is placed into the metastable state during which fluid may pass in the single flow path through both the first and second valves;
    b) applying a second force to either of the first or second arms, wherein the dual latching valve is removed from the metastable state, and wherein at least one of the first and second valves in the single flow path is closed.

2. The method of claim 1, wherein the first force is applied by an external source.

3. The method of claim 1, wherein the step of applying the first force to either of the first or second arms further comprises a step of placing the first or second arm at a rest position on an interference mechanism.

4. The method of claim 3, wherein the interference mechanism comprises a lip, an edge, or a groove, and the step of applying the first force to either of the first or second arms comprises a step of positioning the first or second arm at the lip, edge, or groove of the interference mechanism.

5. The method of claim 4, wherein an interference feature comprises a slope or a taper, and the step of applying the second force to the same one of the first or second arms comprises a step of pulling the same one of the first or second arms away from the interference mechanism using the interference feature.

6. The method of claim 3, wherein the step of applying the second force to one of the first or second arms comprises a step of removing an interference feature.

7. The method of claim 1, wherein the step of applying the first force to either of the first or second arms comprises a step of placing a removable obstruction into the dual latching valve.

8. The method of claim 7, wherein the step of applying the second force to one of the first or second arms comprises a step of removing the removable obstruction from the dual latching valve.

9. The method of claim 1, wherein the step of applying the first force to either of the first or second arms comprises a step of moving a valve seat at either the first or second arms away from the corresponding one of the first or second arms.

10. The method of claim 9, wherein the step of applying the second force to the first or second arms comprises a step of sliding or snapping the valve seat into position.

11. A dual-latching valve operable in a metastable state, comprising:
    a) first and second compressible tubes, the first compressible tube positioned at a first position in a flow path and the second compressible tube positioned at a different second position in the same flow path;
    b) first and second valve arms positioned adjacent to the first and second tubes, respectively, and thereby forming first and second valves;
    c) a valve mechanism operable to selectively open and close the first and second valves by selectively engaging with the first and second valve arms wherein only one of the first and second valves is open at a time; and
    d) an interference mechanism positioned to engage at least one of the first and second valve arms whereby the dual latching valve enters the metastable state allowing fluid flow simultaneously through the first and second valves.

12. The dual latching valve of claim 11, wherein the valve mechanism is adapted to receive at least the first or second valve arm to form the interference mechanism in order to create the metastable state.

13. The dual latching valve of claim 12, wherein at least one of the first and second valve arm comprises a resilient member or is acted upon by a resilient member.

14. The dual latching valve of claim 13, wherein the resilient member forces the first or second valve arm into a gap created by the movement of the interference mechanism, thereby terminating the metastable state.

15. The dual latching valve of claim 12, wherein the interference mechanism comprises a lip, an edge, or a groove to aid in retention of the metastable state.

16. The dual latching valve of claim 12, wherein the interference mechanism comprises a slope or a taper that aids in the termination of the metastable state.

17. The dual latching valve of claim 12, wherein stable operation of the valve moves the interference mechanism to create a gap that is wider than the valve arm.

18. The dual latching valve of claim 12, wherein the valve mechanism is configured to be movable out of the way, thereby terminating the metastable state.

19. The dual latching valve of claim 18, wherein the valve mechanism is configured to first close one valve and then release the second valve arm to terminate the metastable state.

20. The dual latching valve of claim 19, wherein the valve mechanism comprises a cam.

21. The dual latching valve of claim 11, wherein the interference mechanism comprises a removable obstruction configured to place the valve in a metastable state.

22. The dual latching valve of claim 21, wherein the removable obstruction is further configured to terminate the metastable state when removed from the valve.

23. The dual latching valve of claim 11, wherein the interference mechanism comprises a moveable valve seat configured to relieve compression of at least the first or second tube.

24. The dual latching valve of claim 23, further comprising a valve seat, wherein sliding or snapping the valve seat into position with a locking mechanism terminates the metastable state.

* * * * *